(12) United States Patent
Irion et al.

(10) Patent No.: US 7,108,657 B2
(45) Date of Patent: Sep. 19, 2006

(54) ENDOSCOPIC VISUALIZATION APPARATUS WITH DIFFERENT IMAGING SYSTEMS

(75) Inventors: Klaus M. Irion, Liptingen (DE); Karl Christian Storz, Tuttlingen (DE)

(73) Assignee: Karl Storz GmbH & Co. KG, (DE)

( * ) Notice: Subject to any disclaimer, the term of this patent is extended or adjusted under 35 U.S.C. 154(b) by 215 days.

(21) Appl. No.: 10/674,454

(22) Filed: Sep. 30, 2003

(65) Prior Publication Data

US 2004/0122290 A1    Jun. 24, 2004

Related U.S. Application Data

(63) Continuation of application No. PCT/EP02/03519, filed on Mar. 28, 2002.

(30) Foreign Application Priority Data

Mar. 30, 2001    (DE) ................... 101 16 056

(51) Int. Cl.
*A61B 1/05*    (2006.01)
*A61B 1/045*    (2006.01)

(52) U.S. Cl. ............ 600/110; 600/109; 600/173; 600/111; 600/171; 348/76

(58) Field of Classification Search ............ 600/113, 600/111, 166, 173, 170, 171, 168, 110; 348/45, 348/76
See application file for complete search history.

(56) References Cited

U.S. PATENT DOCUMENTS

| | | | | |
|---|---|---|---|---|
| 3,889,662 A | | 6/1975 | Mitsui | .................. 128/6 |
| 4,588,294 A | * | 5/1986 | Siegmund | .................. 600/117 |
| 4,838,247 A | * | 6/1989 | Forkner | .................. 600/173 |
| 4,873,572 A | * | 10/1989 | Miyazaki et al. | .................. 348/45 |
| 4,875,099 A | * | 10/1989 | Sakai et al. | .................. 358/483 |
| 4,926,257 A | * | 5/1990 | Miyazaki | .................. 348/45 |
| 5,166,787 A | | 11/1992 | Irion | .................. 358/98 |
| 5,178,130 A | * | 1/1993 | Kaiya | .................. 600/109 |
| 5,603,687 A | * | 2/1997 | Hori et al. | .................. 600/166 |
| 5,797,835 A | | 8/1998 | Green | .................. 600/106 |
| 5,989,185 A | * | 11/1999 | Miyazaki | .................. 600/175 |
| 6,036,637 A | * | 3/2000 | Kudo | .................. 600/173 |
| 2002/0114071 A1 | * | 8/2002 | Igarashi | .................. 359/462 |

FOREIGN PATENT DOCUMENTS

| | | |
|---|---|---|
| DE | 2 425 827 | 12/1974 |
| DE | 38 06 190 A1 | 9/1988 |
| DE | 42 41 938 A1 | 6/1994 |
| DE | 101 16 056 A1 | 10/2002 |
| WO | WO 95/26674 | 10/1995 |
| WO | WO 96/39916 | 12/1996 |

* cited by examiner

*Primary Examiner*—John P. Leubecker
(74) *Attorney, Agent, or Firm*—St. Onge Steward Johnston & Reens LLC

(57) ABSTRACT

An endoscopic visualization apparatus has a first imaging system and at least one second imaging system, a first image field being covered by the first imaging system, and a second image field being covered by the second imaging system. The first imaging system and the second imaging system are arranged in a common housing. The first imaging system and the second imaging system are significantly different with regard to at least one optical parameter, and the first image field and the at least one second image field overlap one another only partially.

9 Claims, 3 Drawing Sheets

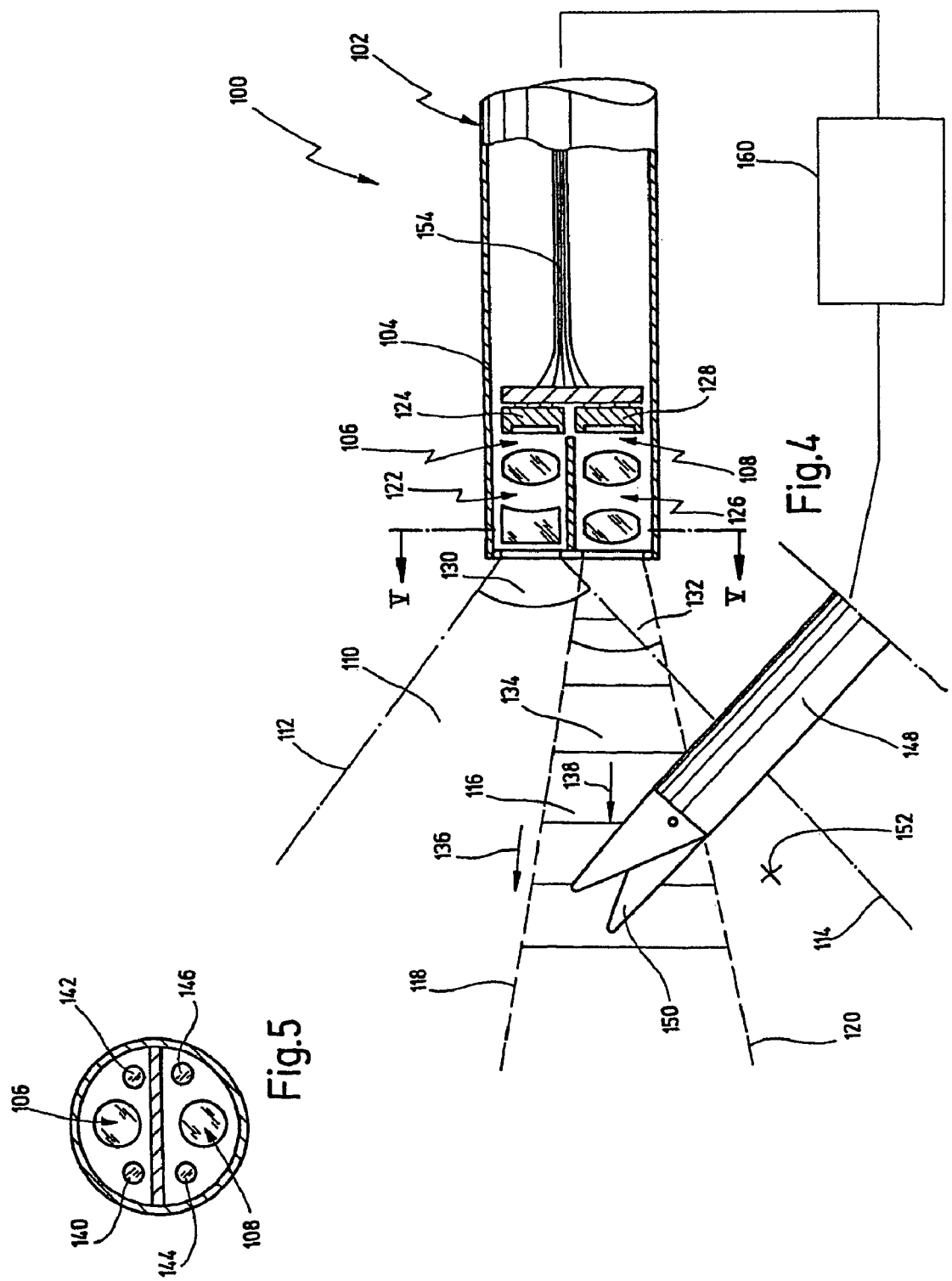

ENDOSCOPIC VISUALIZATION APPARATUS WITH DIFFERENT IMAGING SYSTEMS

CROSS-REFERENCE TO PENDING APPLICATION

The present application is a continuation of pending international patent application PCT/EP 02/03519 filed on Mar. 28, 2002 which designates the United States and which claims priority of German patent application 101 16 056.9 filed on Mar. 30, 2001.

BACKGROUND OF THE INVENTION

The invention relates to an endoscopic visualization apparatus having a first imaging system and having at least one second imaging system, a first image field being covered by the first imaging system, and a second image field being covered by the second imaging system, and the imaging systems being arranged in a common housing.

An endoscopic visualization apparatus of the type mentioned at the beginning is used, for example, as an observation system for medical purposes in what is termed minimally invasive surgery. In the case of standard operations such as, for example, laparoscopic cholecystectomy, access is usually made to the abdominal cavity via three small incisions artificially created in the abdominal wall. One of the three openings serves for introducing the visualization apparatus, for example an endoscope, while the operating instruments, for example tubular shaft instruments, are introduced into the abdominal cavity via the two other openings. The surgical operation is executed by the instruments guided by the surgeon, under visual control via the monitor on which the image supplied by the endoscopic visualization apparatus is displayed. The endoscopic visualization apparatus itself is operated by the assistant staff and controlled in terms of position such that the operating area of the operating instruments is always located in the image field of the visualization apparatus.

There is often the wish to display the operating area on the monitor in an enlarged fashion or from another viewing angle. In order to be able to display the operating area in an enlarged fashion, it is known to use a zoom objective which can be set from the proximal end or distal end, or the endoscope is displaced axially for this purpose. In order to display the operating area from another viewing angle, it is necessary to make consecutive use of various endoscopes with different directions of view. Both the setting of a zoom objective, the axial displacement of the endoscope and the changing of various endoscopes constitute additional manipulations, and thus an additional outlay, and so the operating times are lengthened and the costs of operations are raised because of additional visualization apparatuses.

However, there are known in the prior art arrangements which offer multiple display of the operating area, and thus a remedy with regard to the disadvantages mentioned above.

DE 38 06 190 A1 discloses an electronic endoscope device which comprises an elongated insertion part, two imaging optical systems in the form of two objectives at the distal end of the insertion part, and an imaging apparatus in the form of an electronic imager which is assigned to the two objectives. A stereo view can be obtained with the aid of this known endoscopic visualization apparatus. This endoscopic visualization apparatus therefore comprises two imaging systems which respectively cover an image field. The image fields covered by the two imaging systems are, however, substantially identical and overlap one another essentially completely. The two objectives of the two imaging systems, and thus the latter themselves, are identical for this purpose with regard to their optical properties. The two imaging systems differ from one another only slightly in their directions of view, something which is also necessary so that the two juxtaposed imaging systems cover the same image field in order to obtain a three-dimensional impression of this image field.

An endoscopic visualization apparatus comparable thereto is disclosed in DE 42 41 938 A1, which describes an endoscope with stereo side-viewing optics. In the case of this known visualization system, as well, the image fields of the two imaging systems overlap one another virtually completely, and the imaging systems do not differ from one another with regard to their imaging properties, in order precisely to convey a stereo image or a three-dimensional impression of an observed object. Apart from this stereoscopic information, it is not possible in the case of the two known visualization apparatuses previously mentioned to obtain further image information relating to the operating area.

Furthermore, U.S. Pat. No. 5,166,787 discloses a video endoscope which, in accordance with an exemplary embodiment, has two imaging systems comprising in each case an objective and an electronic imager. In accordance with a variant of this known endoscope, the two imaging systems are capable of producing a stereoscopic effect in which the two imaging systems are pivoted into a position in which the two imaging systems cover two image fields which, once again, overlap one another virtually completely. In accordance with a further alternative, two imaging systems are present in the endoscope, their directions of view differing by 180° such that the image fields covered by the two imaging systems are completely disjunct. Although an overall image field which is larger as a whole is thereby achieved, it is not possible to obtain any additional image information from one and the same observed area. Apart from this, in the case of this endoscope the undesired manipulations already previously mentioned are required in order to move the two imaging systems into the appropriate active position.

It is therefore the object of the invention to develop an endoscopic visualization apparatus of the type mentioned at the beginning to the extent that it is possible to obtain more image information with one and the same visualization apparatus without the need for this purpose of manipulations of the visualization apparatus or even a change of the visualization apparatus.

SUMMARY OF THE INVENTION

According to the invention, an endoscopic visualization apparatus is provided, comprising:
a housing;
a first imaging system covering a first image field, said first imaging system being arranged in said housing;
a second imaging system covering a second image field, said second imaging system being arranged in said housing,
wherein said first imaging system and said second imaging system are significantly different with regard to at least one optical parameter, and wherein said first image field and said at least one second image field overlap one another only partially.

The endoscopic visualization apparatus according to the invention differs from the purely stereoscopic visualization systems in that the first image field and the at least one second image field overlap only partially such that the image fields cover different areas of coverage. The visualization apparatus according to the invention differs from the known endoscopic visualization apparatus, in which the two imaging systems cover completely different, that is to say disjoint image fields, in that the at least two image fields overlap at least partially. In the partial overlap area of the image fields covered by the at least two imaging systems, it is possible to obtain not only stereoscopic image information but, in addition, further image information, for example whenever the two imaging systems differ with regard to their aperture angle as optical parameter, as is provided in a preferred refinement described below. By contrast with the pure stereo visualization systems, the only partial overlapping of the at least two image fields covers an overall larger image region, as a result of which it is like-wise possible to obtain further additional image information. In other words, the endoscopic visualization apparatus according to the invention creates a "multivisual" visualization system which permits additional image information to be obtained without additional manipulations by the assistant staff and without increased outlay on instrumentation. Whereas a difference based on tolerances can possibly occur between the optical parameters of the two imaging systems in the case of stereo endoscopic systems, the aim is for the imaging systems of the visualization apparatus according to the invention to differ significantly from one another with regard to at least one optical parameter.

In a preferred refinement, the first imaging system differs from the at least one second imaging system with regard to the direction of view.

In the case of this refinement, the advantage consists in that by contrast with the conventional stereoscopic visualization units a larger overall image field is obtained as a whole, it being possible to obtain stereoscopic, that is to say three-dimensional information from an observed object in the partial overlap region. The directions of view are also not only slightly different and mutually conjugate, as in the case, for example, of stereo endoscope systems, but differ significantly from one another, again. By contrast with stereoendoscopes, the directions of view can also be selected such that they have no point of intersection in the overall image field, that is to say they diverge, with the proviso that the image fields overlap partially.

In a further preferred refinement, the first imaging system differs from the at least one second imaging system with regard to the aperture angle.

This refinement advantageously combines with one another two imaging systems with different imaging properties to form one and the same visualization apparatus, the imaging properties being manifested in a different magnification of the observed image. A zoom objective, such as is provided in the prior art and which must be appropriately set by the assistant staff, can therefore be omitted in the case of the visualization apparatus according to the invention. In particular, in the overlap region of the two image fields the quasi-stereoscopic image information obtained there is supplemented by a further item of image information which results from different zoom factors. It is advantageously possible in this way to use the visualization apparatus according to the invention to measure objects and to measure distances between the visualization apparatus and an object, for example tissue in the human body.

Of course, the previously mentioned refinement, in accordance with which the first imaging system differs from the at least one second imaging system with regard to the aperture angle, can also be combined with the previously mentioned refinement in accordance with which the first imaging system differs from the at least one second imaging system with regard to the direction of view. The gain in information for the image obtained is thereby increased still further. Moreover, it goes without saying that it is possible to integrate not only two different imaging systems, but also three or more different imaging systems, in the way previously mentioned into one and the same visualization apparatus if this is possible for reasons of space. It is to be taken into account here that endoscopic visualization apparatuses for use in minimally invasive surgery are intended to fulfil particular requirements placed on the maximum overall size.

In a further preferred refinement, the first imaging system has a first objective on the distal end, and the at least one second imaging system has a second objective on the distal end, and the first objective differs significantly from the second objective with regard to the at least one optical parameter.

This measure is advantageous not only when the endoscopic visualization apparatus has at least two imaging systems based on electronic imagers, but also when the endoscopic visualization apparatus has at least two imaging systems based on relay lens systems or ordered fibre bundles for image transmission. To be precise, in the latter case, it is possible on the basis of the previously mentioned measure to configure the two imaging systems identically except for the different objectives, thus advantageously reducing the design outlay.

It is particularly preferred in this context when the first objective is assigned a first electronic imager and the second objective is assigned a second electronic imager.

Whereas the present invention, as previously mentioned, can also be used in the case of endoscopic visualization apparatuses with imaging systems based on optical image transmission systems, the previously mentioned measure has the particular advantage that the overall visualization apparatus can be configured to be very narrow overall, which is always required for medical applications. In order to integrate at least two imaging systems based on optical image transmission systems in a standard endoscope, there would specifically be a need for the two image transmission systems to be of very thin design, which is associated with a corresponding loss in quality of the image transmission. By contrast, miniaturized electronic imagers are already currently available with maximum diameters of less than 3 mm which permit the use of a plurality of such systems in an endoscope.

It is preferred in this case when for the second and, if appropriate, each further imager only in each case one additional signal line for video image transmission leads from distal to proximal end, while the signals for reading out and for the voltage supply of the imagers are used jointly for all imagers.

In the case of such a connection of the electronic imagers, it is possible to manage with only one drive circuit and the same number of supply leads for the voltage supply for the purpose of readout, and for the clock signals of the imagers, as for a single electronic imager, there then being a need for only in each case one additional cable per imager as signal line for the video output signal.

In order to permit an image erection of the observed image, the first imager and/or the second imager can preferably be rotated about an axis transverse to the image recording surface.

However, an image erection can also be implemented via appropriate data processing in the image processing unit, to which the video output signals are fed.

In a further preferred refinement, the imaging systems are assigned at least one illuminating system which radiates light such that each image field is illuminated.

This measure has the advantage that all the image fields covered by the imaging systems are adequately illuminated in accordance with the previously mentioned refinements, and it is ensured that all the additionally obtained image information is utilized.

In a further preferred refinement, a positioning device is provided for automatically tracking the visualization apparatus as a function of a position of an operating instrument, the positioning device acting such that the operating instrument always appears in one of the image fields.

This refinement is particularly advantageous in conjunction with the above-named refinement in accordance with which the at least two imaging systems differ with regard to their aperture angle. The positioning device can, for example, be designed such that tracking of the visualization apparatus is performed when the operating instrument moves out of the zoomed image of the one imaging system with a relatively small aperture angle into the overall image of the imaging system with a larger aperture angle such that the operating instrument always appears in the image field of the imaging system of smaller aperture angle.

the image of larger aperture angle can serve the surgeon as overall image for the purpose of better orientation in the operating space, while the image field of smaller aperture angle, and thus a larger image, permits a more highly resolving observation of the tip of the operating instrument and of the tissue located in its vicinity.

In a preferred refinement, the visualization apparatus according to the invention can be designed in the form of an endoscope, the at least two imaging systems being arranged in a distal end of a shaft of the endoscope. Particularly in conjunction with the refinement of the imaging systems with electronic imagers, the shaft can advantageously be of very narrow overall design.

As an alternative to this, it is likewise preferred when the endoscopic visualization apparatus is designed in the form of a video camera unit which has at least two imaging systems in accordance with one or more of the previously mentioned refinements, which video camera unit is fastened on a guide shaft for guiding an operating instrument.

It is possible by means of this refinement to reduce the number of incisions to be made in the body surface during a minimally invasive operation when the endoscopic visualization apparatus is fastened on the guide shaft through which the operating instrument is inserted into the operating area. It is also possible thereby to implement a very simple, in particular mechanically acting positioning device for the tracking of the visualization apparatus as a function of the position of the operating instrument.

Further advantages emerge from the following description and the attached drawing.

It goes without saying that the previously mentioned features and those which are still to be explained below can be used not only in the combination respectively specified, but also in other combinations or on their own, without departing from the scope of the present invention.

BRIEF DESCRIPTION OF THE DRAWINGS

Exemplary embodiments of the invention are illustrated in the drawing and are described in further detail here with reference to the latter, in which:

FIG. 4 shows a longitudinal section through a distal end of an endoscopic visualization apparatus in an exemplary embodiment modified by comparison with FIGS. 2 and 3; and FIG. 5 shows a section along the line V—V in FIG. 4.

DETAILED DESCRIPTION OF PREFERRED EMBODIMENTS

Figure 1:
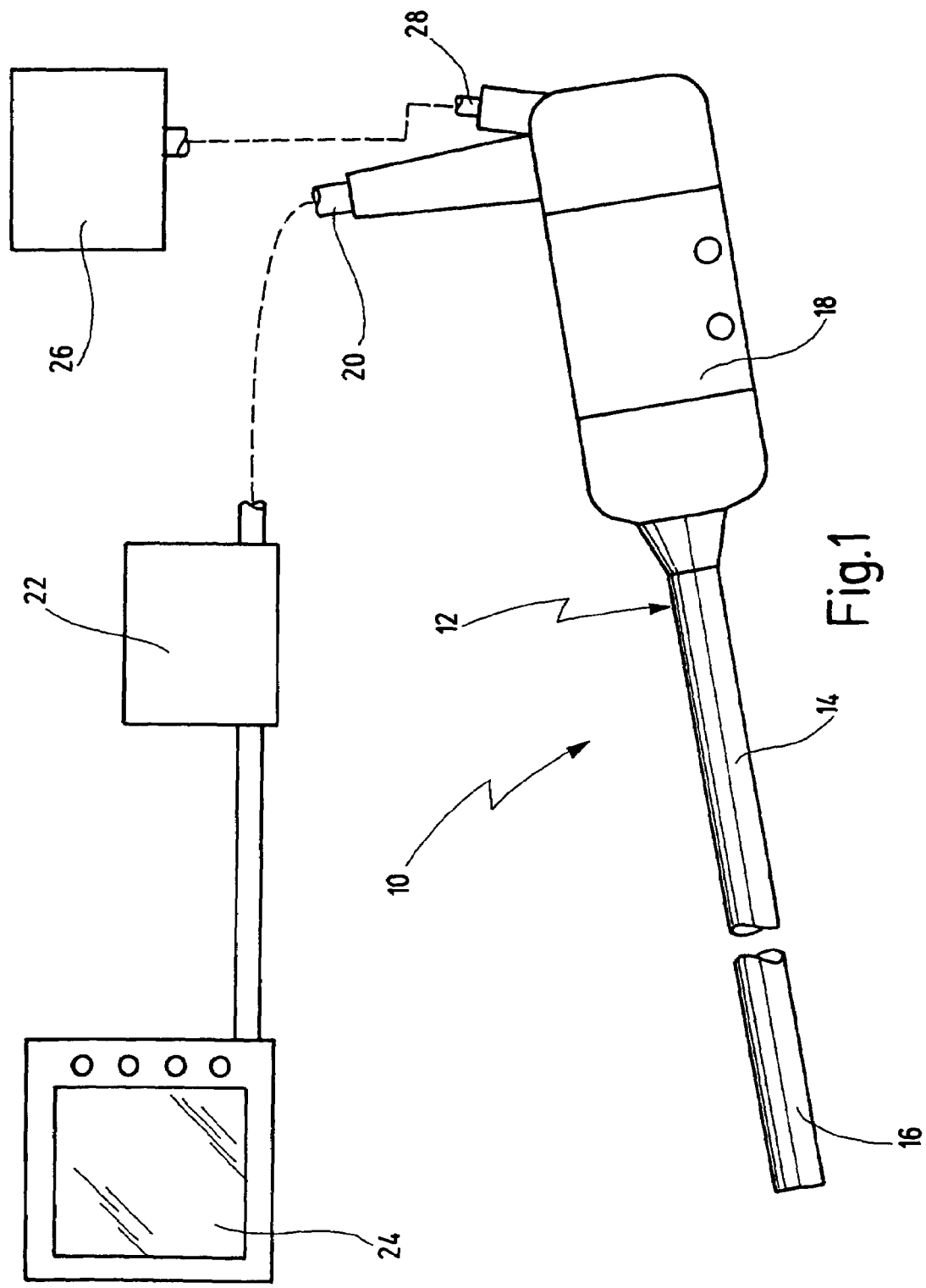
FIG. 1 shows an endoscopic visualization apparatus in an overall representation, and its connection to peripherals.

An endoscopic visualization apparatus provided with the general reference numeral 10 is illustrated in FIG. 1. The endoscopic visualization apparatus 10 is designed in the form of an endoscope 12 in the exemplary embodiment shown.

The endoscopic visualization apparatus 10 in the form of the endoscope 12 is used in the field of minimally invasive surgery.

The endoscope 12 has an elongated shaft whose distal end section or distal end is provided with the reference numeral 16.

In the exemplary embodiment shown, the shaft 14 is designed to be rigid overall, but the present invention can equally well be used in the case of a flexible endoscope with a correspondingly flexible shaft.

The endoscope 12 is designed, furthermore, as a video endoscope and therefore does not have an eyepiece at the proximal end of the shaft 14, but a handpiece 18. A cable 20 leads from the handpiece 18 for the purpose of electric signal transmission to an image processing unit 22 which is connected, in turn, to a monitor 24 for displaying endoscopic images which are supplied by the endoscope 12.

Also provided is a light source 26 which generates light which is fed into the endoscope 12 through the handpiece 18 into the shaft 14 and up to the distal end 16. The light source 26 is connected correspondingly to the handpiece 18 of the endoscope 12 via an optical-fibre cable 28.

Figures 2, 3:
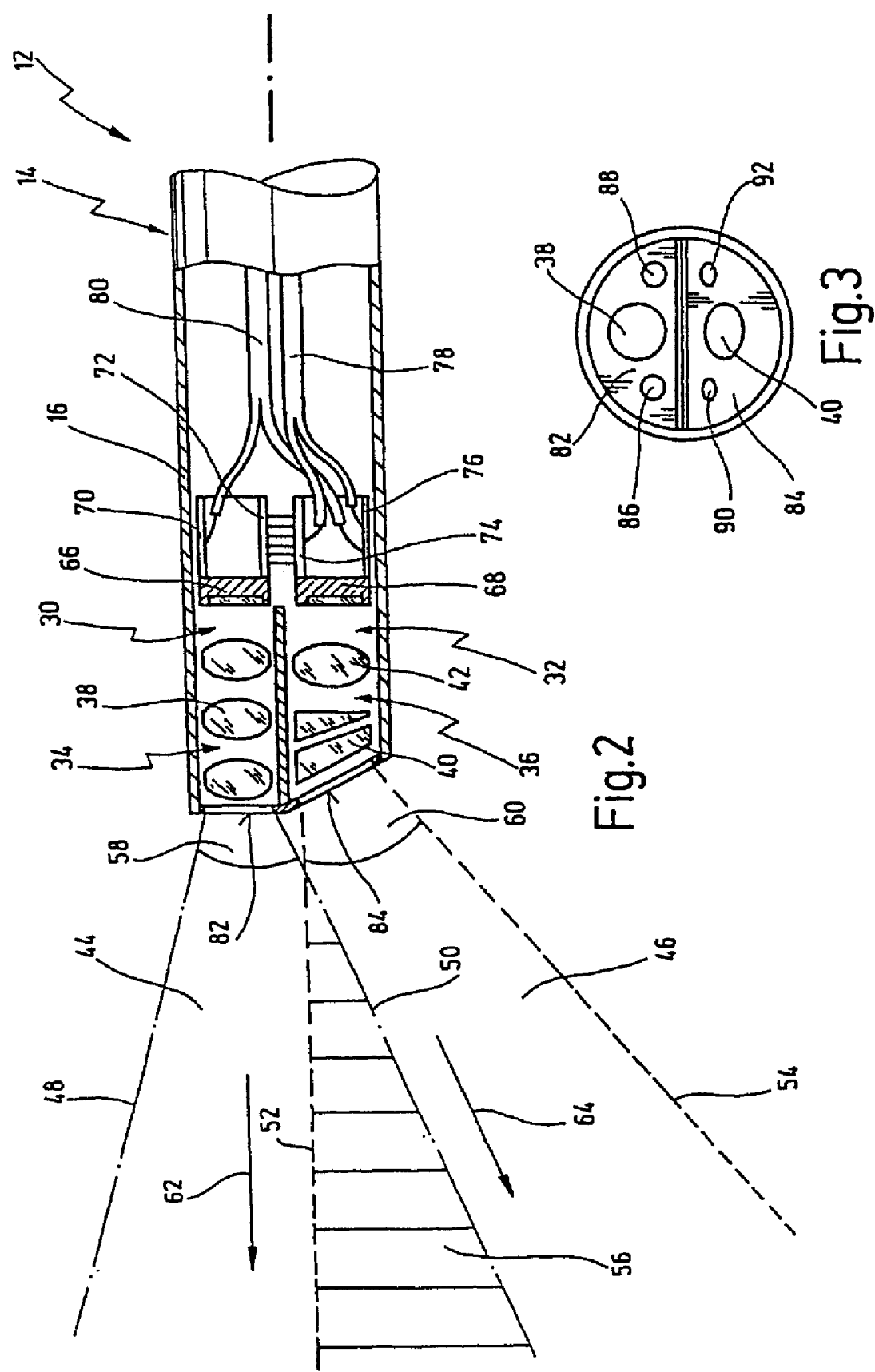
FIG. 2 shows a longitudinal section through the distal end of the endoscopic visualization apparatus in FIG. 1, on an enlarged scale by comparison with FIG. 1.
FIG. 3 shows a front view of the distal end of the endoscopic visualization apparatus in FIG. 2.

The distal section 16 of the shaft 14 of the endoscope 12 is illustrated on an enlarged scale with further details in FIGS. 2 and 3.

A first imaging system 30 is arranged in the shaft 14, and a second imaging system 32 is arranged in parallel with the first.

The first imaging system 30 has a first objective 34, while the second imaging system 32 has a second objective 36. The first objective 34 comprises an arrangement (illustrated here only by way of example and symbolically) composed of lenses 38, while the second objective 36 has an arrangement (which is also to be understood here purely as exemplary) composed of two prisms 40 and a lens 42.

The symbolic illustration of the objectives 34 and 36 is intended here to illustrate that the two objectives 36 and 38 have different optical parameters.

The optical parameters of an endoscopic visualization apparatus determine the image field covered by the corresponding imaging system, and the image information obtained therefrom. The image field covered, including the image information obtained therefrom, is determined in the case of an endoscopic visualization system by the direction of view as the first optical parameter, and by the aperture angle as the second optical parameter.

An image field covered by the first imaging system 30 is provided with the reference numeral 44, while an image field covered by the second imaging system 32 is provided with the reference numeral 46. The boundary of the first image field 44 is illustrated by dashed and dotted lines 48 and 50, while the boundary of the second image field 46 is illustrated by broken lines 52 and 54.

The first imaging system 30 and the second imaging system 32, that is to say more precisely the first objective 34 and the second objective 36 are now designed and/or oriented such that the first image field 44 and the second image field 46 overlap only partially, a corresponding overlap region being provided with the reference numeral 56 (hatched in FIG. 2).

An aperture angle of the first imaging system 30 is provided with the reference numeral 58, while an aperture angle of the second imaging system 32 is provided with the reference numeral 60. A direction of view of the first imaging system 30 is illustrated by an arrow 62, and a direction of view of the second imaging system 32 is illustrated by an arrow 64.

In the exemplary embodiment, illustrated in FIGS. 2 and 3, of the endoscope 12 in FIG. 1, the first imaging system 30 and the second imaging system 32 differ with regard to the directions of view 62 and 64. The first imaging system 30 has a direction of view of approximately 0°, referred to the longitudinal axis of the shaft 14, while the direction of view 64 of the second imaging system 32 encloses an angle of approximately 30° with the longitudinal axis of the shaft 14. The directions of view 62 and 64 diverge in this exemplary embodiment. By contrast, the aperture angles 58 and 60 do not differ from one another in the exemplary embodiment illustrated in FIGS. 2 and 3. Apart from the previously mentioned directions of view, it is also possible to use other directions of view within the scope of the invention, for example 0° and 60°, 30° and 60°, 60° and 90°, etc, as long as the assigned image fields overlap at least partially, but not completely and the directions of view differ significantly.

The endoscope 12 therefore integrates in a single endoscope two imaging systems with different directions of view and the same aperture angle. It is possible to obtain from the overlap region 56 of the two image fields 44 and 46 stereoscopic image information of an object located therein, that is to say this object can be seen in three dimensions in the overlap region 56. The overall image of the two imaging systems 30 and 32, which is bounded by the lines 48 and 54 in FIG. 2, is substantially enlarged, however, by contrast with a conventional stereo endoscope, in the case of which the two image fields overlap one another completely.

The first imaging system 30 and the second imaging system 32 further each have an electronic imager 66 and 68, respectively, onto which the respective objective 34 and 36, respectively, is imaged. The direct assignment of the imagers 66 and 68 to the objectives 34 and 36, that is to say the distal-end arrangement of the imagers 66 and 68, has the advantage that optical transmission systems such as optical fibres or relay lens systems, which require an appropriate diameter in order to ensure a satisfactory transmission quality, are not required. However, it is likewise possible within the scope of the present invention to arrange the imagers 66 and 68 at the proximal end of the endoscope, for example in the handpiece 18, and to provide for light to be transmitted starting from the objectives 34 and 36, respectively, through optical fibres and the like to the imagers.

The imagers 66 and 68 are designed in conjunction with a tape automated bonding (TAB) package in the case of which the connecting pads 70 and 72 of the first imager 66 and the connecting pads 74 and 76 of the second imager 68 are connected in a mirror-image fashion relative to one another. It is therefore possible to make direct mutual contact between the pads 72 and 74, as illustrated in FIG. 2. Consequently, the two imagers 66 and 68 can be driven via a common supply lead, while only the video output signals run separately and are tapped correspondingly at the pads 70 and 76. Corresponding electric lines are provided with the reference numerals 78 and 80.

At least one of the imagers 66 and 68 can be rotated about an axis which runs parallel to the longitudinal central axis of the shaft 14 and runs transverse to the frontal image recording surface of the corresponding imager 66 or 68, in order to erect one of the two images corresponding to the image fields 44 and 46, respectively, or to adapt it appropriately to the other image field. Instead of the rotatability of the imagers 66 and/or 68, it is also possible to erect the image appropriately in the image processing unit 22.

Surfaces 82 and 84 of the imaging systems 30 and 32 which are on the light entry side are inclined to one another at an angle of approximately 30° in accordance with the different directions of view 62 and 64. Each of the imaging systems 30 and 32 is assigned a corresponding illuminating system, the illuminating system comprising a first optical fibre 86 and a second optical fibre 88 whose end at the light exit side lies in the surface 82 such that the optical fibres 86 and 88 radiate light generated by the light source 26 into the image field 44. The illuminating system correspondingly has two further optical fibres 90 and 92, which open into the surface 84 and are consequently directed such that they illuminate the image field 46 completely.

Instead of one or more optical fibres as in FIG. 3, it is also possible to arrange at an appropriate site light sources such as light emitting diodes which are fed as appropriate via an electric supply lead from the proximal end.

A further exemplary embodiment of an endoscopic visualization apparatus is illustrated in FIGS. 4 and 5, this endoscopic visualization apparatus being designed, in turn, in the form of an endoscope 100 comparable to the endoscope 12. The endoscope 100 has a shaft 102 in whose distal section 104 a first imaging system 106 and a second imaging system 108 are arranged.

The first imaging system 106 covers a first image field 110, whose boundaries are illustrated by lines 112 and 114, while the second imaging system 108 covers a second image field 116, whose boundary is illustrated by lines 118 and 120, respectively. The first imaging system 106 has a first objective 122 and a first electronic imager 124, and the second imaging system 108 has a second objective 126 and a second imager 128.

The first imaging system 106 and the second imaging system 108 differ, in turn, from one another with regard to at least one optical parameter, specifically in the present case with regard to their aperture angle 130 and 132, respectively. The aperture angle 130 of the first imaging system 106, which is prescribed by the first objective 122, is larger in this case than the aperture angle 132 of the second imaging system 108, which is determined by the objective 126 thereof.

The corresponding image fields 110 and 116 covered by the imaging systems 106 and 108 overlap one another only partially, as in the preceding exemplary embodiment. A corresponding overlap region is illustrated in a hatched fashion in FIG. 4 and provided with the reference numeral 134.

An object located in the overlap region 134 is seen in a magnified fashion by the second imaging system 108 with the smaller aperture angle 132, such that the second imaging system 108 amounts to a zoom objective, while the same object in the overlap region 134 appears simultaneously in the image field 110 of the first imaging system 106 with the larger aperture angle, as a result of which this image information can be used for the purpose of detecting the position of the object with reference to the surroundings in the operating area in the sense of an overall image.

Thus, with this refinement it is possible to use only the one endoscope 100 to obtain from one and the same object an overall (total) image, on the one hand, and a magnified image, on the other hand. Moreover, quasi-stereoscopic effects are produced in the overlap region 134 of the image fields 110 and 116 which permit a three-dimensional exact coverage of the geometry of the observed object and also a measurement of the spacing between the distal end 104 of the endoscope 100 and the object.

The aperture angle 130 of the first imaging system 106 is 75°, for example, and the second aperture angle 132 of the second imaging system 108 is 40°, for example.

Whereas the objectives 122 and 126 in FIG. 4 have a direction of view of approximately 0° relative to the longitudinal axis of the shaft 102, as indicated by arrows 136 and 138, it is also possible, however, to provide appropriate objectives with the same aperture angle but different directions of view.

It goes without saying that the exemplary embodiment in accordance with FIG. 4 can be combined with the exemplary embodiment in accordance with FIG. 2, that is to say two or more imaging systems with both different aperture angles and different directions of view can be combined with one another into one and the same visualization apparatus.

In accordance with FIG. 5, the imaging systems 106 and 108 are assigned, in turn, at least one illuminating system in the form of optical fibres 140 to 146 which ensures appropriate illumination of the image fields 110 and 116. In order, in accordance with the larger aperture angle 130 of the imaging system 106, to ensure adequate illumination of the image field 110, the optical fibres 140 and 142 are, for example, assigned appropriate expansion optics.

Also shown in FIG. 4 is an operating instrument 148 whose distal tip 150 is situated simultaneously in the image field 116 of the second imaging system 108, and simultaneously in the first image field 110 of the first imaging system 106, in other words in the overlap region 134 of the two image fields 110 and 116.

Provided for the purpose of automatic tracking of the visualization apparatus or of the endoscope 100 is a positioning device 160 which tracks the endoscope 100 as a function of the position of the operating instrument 148, for example as a function of the position of the tip 150 of the operating instrument 148, in such a way that the tip 150 of the operating instrument 148 always appears in the second image field 116, in which the tip 150 of the operating instrument 148 is imaged in a magnified fashion.

If, when being manipulated, the operating instrument 148 moves during a surgical operation in such a way that the tip 150 comes to lie outside the image field 116, for example at a site provided with the reference numeral 152, the positioning device 160 becomes active and tracks the endoscope 100 such that the tip 150 appears again in the image field 116, that is to say in a magnified fashion. As long as the tip 150 appears in the image field 116, the positioning device 160 is inactive, that is to say a movement of the tip 150 in the image field 116 preferably does not lead to tracking of the endoscope 100. The positioning device 160 has appropriate position sensors in order appropriately to detect the position of the tip 150 of the operating instrument 148. The positioning device 160 can be controlled as appropriate by the image processing unit.

It is also illustrated in FIG. 4 that contact is made with the imagers 124 and 128 on a common pad, that is to say a common circuit board, only one supply lead for feeding the imagers being required for both imagers 124 and 128, while the video output signals must be led proximally in an appropriately separated fashion to the image processing unit 22. Appropriate lines 154 are illustrated in FIG. 4.

As already mentioned, the exemplary embodiments of FIGS. 2 and 3 and 4 as well as 5 can be combined with one another. Moreover, it is also possible for more than two imaging systems to be integrated in an endoscopic visualization apparatus, it thereby being possible to raise still further the information content obtained for the endoscopic images.

Whereas the endoscopic visualization apparatus is designed in each case in the exemplary embodiments in the form of an endoscope, the endoscopic visualization apparatus can, however, also have a video camera unit which has the at least two imaging systems, and which is fastened on a guide shaft for guiding an operating instrument such as that of the operating instrument 148 in FIG. 4. It is possible in this way to achieve a mechanical coupling between the endoscopic visualization apparatus and the operating instrument which renders possible a simple way of automatically tracking the endoscopic visualization apparatus as a function of the position of the operating instrument. Such a video camera unit with at least two imaging systems can correspond in principle to the design of the distal ends 16 and 104, respectively, of the endoscopes 12 and 100 in the likewise miniaturized design.

What is claimed is:

1. An endoscopic visualization apparatus, comprising:
a housing;
a first imaging system covering a first image field, said first imaging system being arranged in said housing and having a first electronic imager;
at least a second imaging system covering a second image field, said second imaging system being arranged in said housing and having a second electronic imager,
wherein said first imaging system and said second imaging system are significantly different with regard to at least one optical parameter, and wherein said first image field and said second image field overlap one another only partially, and
wherein a signal line for reading out and for the voltage supply of said imagers are jointly used by said first imager and said second imager, and wherein said first imager is provided with first connecting pads and said second imager is provided with second connecting pads, and wherein said first and second connecting pads are connected in a mirror-image fashion relative to one another and direct mutual contact is made between the first and second connecting pads.

2. The visualization apparatus of claim 1, wherein said first imaging system differs from said second imaging system with regard to a direction of view.

3. The visualization apparatus of claim 1, wherein said first imaging system has a first objective and said second imaging system has a second objective, and wherein said first objective differs significantly from said second objective with regard to at least one optical parameter.

4. The visualization apparatus of claim 3, wherein said first objective is assigned signed said first electronic imager and second objective is assigned said second electronic imager.

5. The visualization apparatus of claim 1, wherein said first and second imagers can be rotated about an axis transverse to an image recording surface of said imagers.

6. The visualization apparatus of claim 1, wherein said imaging systems are assigned at least one illuminating system which radiates light such that each of said image fields is illuminated.

7. The visualization apparatus of claim 1, further comprising a positioning device for automatically tracking said visualization apparatus as a function of a position of an operating instrument, said positioning device being such that said operating instrument always appears in one of said image fields.

8. The visualization apparatus of claim 1, wherein said apparatus is designed in the form of an endoscope, said two imaging systems being arranged in a distal end of a shaft of said endoscope.

9. The visualization apparatus of claim 1, wherein said apparatus is designed in the form of a video camera unit which has at least two imaging systems and which is fastened on a guide shaft for guiding an operating instrument.

* * * * *